United States Patent
McIntosh et al.

(10) Patent No.: US 8,211,165 B1
(45) Date of Patent: Jul. 3, 2012

(54) IMPLANTABLE DEVICE FOR PLACEMENT IN A VESSEL HAVING A VARIABLE SIZE

(75) Inventors: Charles L. McIntosh, Silver Spring, MD (US); Sean D. Chambers, Bloomington, IN (US); Ram H. Paul, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 13 days.

(21) Appl. No.: 12/350,561

(22) Filed: Jan. 8, 2009

Related U.S. Application Data

(60) Provisional application No. 61/019,703, filed on Jan. 8, 2008.

(51) Int. Cl.
*A61F 2/06* (2006.01)
(52) U.S. Cl. .................................... 623/1.24
(58) Field of Classification Search ............... 623/1.24, 623/1.26, 2.14
See application file for complete search history.

(56) References Cited

U.S. PATENT DOCUMENTS

| | | | |
|---|---|---|---|
| 4,553,974 A | 11/1985 | Dewanjee | |
| 4,675,361 A | 6/1987 | Ward, Jr. | |
| 4,861,830 A | 8/1989 | Ward et al. | |
| 4,902,508 A | 2/1990 | Badylak et al. | |
| 5,017,664 A | 5/1991 | Grasel et al. | |
| 5,324,304 A | 6/1994 | Rasmussen | |
| 5,405,381 A | 4/1995 | Olin | |
| 5,413,599 A | 5/1995 | Imachi et al. | |
| 5,554,389 A | 9/1996 | Badylak et al. | |
| 5,589,563 A | 12/1996 | Ward et al. | |
| 5,595,571 A | 1/1997 | Jaffe et al. | |
| 5,624,704 A | 4/1997 | Darouiche et al. | |
| 5,690,642 A | 11/1997 | Osborne et al. | |
| 5,814,061 A | 9/1998 | Osborne et al. | |
| 5,993,844 A | 11/1999 | Abraham et al. | |
| 6,099,567 A | 8/2000 | Badylak et al. | |
| 6,206,931 B1 | 3/2001 | Cook et al. | |
| 6,287,332 B1 | 9/2001 | Bolz et al. | |
| 6,287,334 B1 | 9/2001 | Moll et al. | |
| 6,371,961 B1 | 4/2002 | Osborne et al. | |
| 6,503,272 B2 | 1/2003 | Duerig et al. | |

(Continued)

FOREIGN PATENT DOCUMENTS

WO    WO 01/28459 A1    4/2001

(Continued)

OTHER PUBLICATIONS

John J. Bergan et al., "Chronic Venous Disease", N. Engl. J. Med. 2006; 355: 488-98.

*Primary Examiner* — Thomas J Sweet
*Assistant Examiner* — Tiffany Shipmon
(74) *Attorney, Agent, or Firm* — Buchanan Nipper

(57) ABSTRACT

A device for implantation in a body vessel is provided. The device includes a frame that accommodates dynamic variation in the size of the vessel. At least one leaflet is attached to the frame. The leaflet is deformable between a first position allowing fluid flow in a first, antegrade direction and a second position restricting fluid flow in a second, retrograde direction. Methods for delivering the device to a body vessel and methods and kits for treating a subject using such a device are also provided.

20 Claims, 13 Drawing Sheets

U.S. PATENT DOCUMENTS

| | | |
|---|---|---|
| 6,508,833 B2 | 1/2003 | Pavcnik et al. |
| 6,547,827 B2 | 4/2003 | Carpentier et al. |
| 6,752,826 B2 | 6/2004 | Holloway et al. |
| 6,939,377 B2 | 9/2005 | Jayaraman et al. |
| 7,011,094 B2 * | 3/2006 | Rapacki et al. .......... 128/207.15 |
| 7,070,616 B2 | 7/2006 | Majercak et al. |
| 7,087,089 B2 | 8/2006 | Patel et al. |
| 2001/0039450 A1 | 11/2001 | Pavcnik et al. |
| 2002/0065552 A1 | 5/2002 | Jayaraman et al. |
| 2002/0115559 A1 | 8/2002 | Batchelor et al. |
| 2002/0123802 A1 * | 9/2002 | Snyders ....................... 623/2.18 |
| 2002/0187288 A1 | 12/2002 | Lin et al. |
| 2002/0193828 A1 | 12/2002 | Griffin et al. |
| 2003/0014126 A1 | 1/2003 | Patel et al. |
| 2003/0149471 A1 | 8/2003 | Briana et al. |
| 2003/0208224 A1 * | 11/2003 | Broome ....................... 606/200 |
| 2004/0019374 A1 | 1/2004 | Hojeibane et al. |
| 2004/0034409 A1 | 2/2004 | Heublein et al. |
| 2004/0073297 A1 | 4/2004 | Rohde et al. |
| 2004/0180042 A1 | 9/2004 | Cook et al. |
| 2004/0186558 A1 | 9/2004 | Pavcnik et al. |
| 2004/0224868 A1 | 11/2004 | Meyerhoff et al. |
| 2004/0225352 A1 | 11/2004 | Osborne et al. |
| 2004/0260389 A1 | 12/2004 | Case et al. |
| 2004/0260390 A1 | 12/2004 | Sarac et al. |
| 2005/0096735 A1 * | 5/2005 | Hojeibane et al. ............ 623/1.24 |
| 2005/0096737 A1 * | 5/2005 | Shannon et al. .............. 623/1.44 |
| 2006/0089708 A1 | 4/2006 | Osse et al. .................... 623/1.24 |
| 2006/0212110 A1 * | 9/2006 | Osborne et al. ............... 623/1.24 |
| 2006/0265053 A1 | 11/2006 | Hunt |
| 2007/0027535 A1 | 2/2007 | Purdy et al. |
| 2007/0038295 A1 | 2/2007 | Case et al. |
| 2007/0043431 A1 | 2/2007 | Melsheimer |
| 2007/0093887 A1 | 4/2007 | Case et al. |

FOREIGN PATENT DOCUMENTS

| | | |
|---|---|---|
| WO | WO 03/002165 A1 | 1/2003 |
| WO | WO 03/047468 A1 | 6/2003 |
| WO | WO 2004/080352 A1 | 9/2004 |
| WO | WO 2004/089253 A1 | 10/2004 |
| WO | WO2007067451 * | 6/2007 |

* cited by examiner

IMPLANTABLE DEVICE FOR PLACEMENT IN A VESSEL HAVING A VARIABLE SIZE

RELATED APPLICATIONS

This non-provisional application claims priority to U.S. Provisional Patent Application Ser. No. 61/019,703, filed Jan. 8, 2008, the contents of which are incorporated by reference in their entirety.

TECHNICAL FIELD

The invention relates to implantable medical devices and, more particularly, to artificial valve prostheses and the like.

BACKGROUND

Many vessels in human and animals transport fluids from one body location to another. In some vessels, natural valves are positioned along the length of the vessel to permit fluid flow in a substantially unidirectional manner along the length of the vessel. These natural valves are particularly important in the venous system of the lower extremities to prevent blood from pooling in the lower legs and feet during situations, such as standing or sitting, when the weight of the column of blood in the vein can act to prevent positive blood flow toward the heart. A condition, commonly known as "chronic venous insufficiency", is primarily found in individuals where gradual dilation of the veins, thrombotic events, or other conditions prevent the leaflets of the native valves from closing properly. This leads to significant leakage of retrograde flow such that the valve is considered "incompetent." Chronic venous insufficiency is a potentially serious condition in which the symptoms can progress from painful edema and unsightly spider or varicose veins to skin ulcerations. Elevation of the feet and compression stockings can relieve symptoms, but do not treat the underlying disease. Untreated, the disease can impact the ability of individuals to maintain their normal lifestyle. The mechanism involved in the development of chronic venous disease are reviewed in John J. Bergan et al., "Chronic Venous Disease", N. Engl. J. Med. 2006; 355: 488-98.

A number of surgical procedures have been employed to treat venous valve insufficiency by improving or replacing the native valve. Such procedures include reconstruction of damaged valves with in-situ or exogenous tissue. These efforts have met with limited success and have not been widely adopted as methods of treating chronic venous insufficiency. More recently, efforts have been directed towards finding a suitable self-expanding or otherwise-expandable artificial valve prostheses that can be placed using minimally invasive techniques, rather than requiring open surgery and its obvious disadvantages. Thus far, use of prosthetic venous valves has remained experimental only.

Prosthetic valves have been developed that use a support frame. Frequently, a graft member is attached to the support frame and provides a valve function to the device. For example, the graft member can be in the form of a leaflet that is attached to a frame and movable between first and second positions. In a first position, the valve is open and allows fluid flow to proceed through a vessel in a first direction. In a second position the valve is closed to restrict fluid flow in a second, opposite direction. Examples of such prosthetic valves are described in U.S. Pat. No. 6,508,833, filed Mar. 21, 2001, and U.S. Publication No. 2004/0186558, published Sep. 23, 2004. Another example of a prosthetic valve assembly, including a valve seat and a movable valve composed of a flexible member, is provided by U.S. Pat. No. 5,413,599, filed Dec. 13, 1999. Other known prosthetic valves are attached directly to the vessel wall and do not include a support frame. Examples of such frameless valves are described in U.S. Publication No. 20060265053, published Nov. 23, 2006.

One problem limiting the use of such devices is the potential for thrombus formation, particularly within the valve pockets and other areas where low fluid flow rates can result in pooling and stagnation of blood. Another challenge is the positioning of a device within a body vessel, such as a vein, that dynamically changes its diameter by as such as 50%, due mostly to hydrostatic pressure variations within the fluid within the vessel. For example, such changes within the venous system can occur as a result of everyday activities, such as standing or sitting, or an improvement in patient and/or venous return during treatment.

Other implantable devices, known as self-expanding filters, have been used for temporary or permanent placement within vessels. These devices include a number of anchoring legs diverging from a central hub positioned at one end of the device. For example, such devices have been placed within the vena cava to prevent thrombi or emboli from reaching a patient's lungs and causing a pulmonary embolization. Examples of such devices are described in U.S. Pat. No. 5,324,304, issued Jun. 28, 1994 and U.S. Publication No. 2002/0193828, published Dec. 19, 2002.

SUMMARY

While the invention is defined by the claims appended hereto, additional understanding of the invention can be gained by reference to the attached drawings and the description of preferred embodiments presented below.

One embodiment of the present invention provides a device for implantation in a body vessel. The device includes a hub member and a plurality of flexible struts, each strut having a first end attached to the hub member and a second end. The struts are spring-biased to diverge from the hub member. A frame member extends from one of the struts to a second strut and contacts at least a third of the struts. A leaflet is attached to the frame member and is deformable between a first position allowing fluid flow in a first, antegrade direction and a second position restricting fluid flow in a second, retrograde direction. In one embodiment, the device includes three struts. In one embodiment the hub includes a closed frame defining an aperture.

In another embodiment, at least one of the struts has an anchoring mechanism adapted to engage the wall of the body vessel. The anchoring mechanism can be a barb or a hook.

In one embodiment, the leaflet includes a synthetic biocompatible polymer, cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material, polytetrafluoroethylene, polylactic acid, polyglycolic acid, a polyanhydride, polycaprolactone, polyhydroxy-butyrate valerate, polyhydroxyalkanoate, a polyurethane, naturally derived or synthetic collagenous material, an extracellular matrix material, submucosa, small intestinal submucosa, stomach submucosa, urinary bladder submucosa, uterine submucosa, renal capsule membrane, dura mater, pericardium, serosa, peritoneum or basement membrane materials, liver basement membrane, a mammalian tissue valve, chemically fixed material of a human or non-human primate origin or mixtures or copolymers thereof.

In another embodiment, the leaflet includes an extracellular matrix material or chemically fixed material of a human or non-human primate origin. In yet another embodiment, the extracellular matrix material is small intestinal submucosa.

In another embodiment, the device also includes at least one expanding member connecting to two of the struts between the hub member and the frame member and extending between these struts.

In one embodiment, the hub member is biodegradable and the expanding member is adapted to position the struts against the vessel wall when the hub member degrades. In another embodiment, the hub member includes a biodegradable polymer.

In yet another embodiment, the struts include stainless steel, nickel, silver, platinum, palladium, gold, titanium, tantalum, iridium, tungsten or a self-expanding nickel titanium alloy.

Another embodiment provides a device including a hub member a plurality of flexible struts, each strut having a first end attached to the hub member. A graft sheet is attached to and extends between portions of two of the struts. A leaflet is attached to the graft sheet and is deformable between a first position allowing fluid flow in a first, antegrade direction and a second position restricting fluid flow in a second, retrograde direction.

In one embodiment, the graft sheet includes a biocompatible polymer, cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material, polytetrafluoroethylene, polylactic acid, polyglycolic acid, a polyanhydride, polycaprolactone, polyhydroxy-butyrate valerate, polyhydroxyalkanoate, a polyurethane, naturally derived or synthetic collagenous material, an extracellular matrix material, submucosa, small intestinal submucosa, stomach submucosa, urinary bladder submucosa, uterine submucosa, renal capsule membrane, dura mater, pericardium, serosa, peritoneum or basement membrane materials, liver basement membrane, mammalian tissue, chemically fixed material of a human or non-human primate origin or mixtures or copolymers thereof.

Another aspect of the invention provides a method for regulating fluid flow within a body vessel. The method includes delivering a device as described above to a position within the body vessel within a lumen of a catheter and deploying the device from the lumen so that a proximal end of the device is positioned downstream of flow in an antegrade direction.

Yet another aspect of the invention provides a kit including a delivery catheter and a device as described above

BRIEF DESCRIPTION OF THE DRAWINGS

Embodiments of the present invention will now be described by way of example with reference to the accompanying drawings, in which:

In FIG. 2(a), a leaflet is positioned to restrict flow in a retrograde direction. In FIG. 2(b), a leaflet is positioned to allow flow in an antegrade direction;

FIG. 4(a) shows the device at or just after implantation. The struts are connected to a hub member. FIG. 4(b) shows the device after the hub member as degraded or has been removed. The struts are positioned against the vessel wall.

FIG. 7(a) depicts a device having a hub formed from a cannula of a diameter small enough to fit inside a delivery device. FIGS. 7(b) and 7(c) depict a device having an expandable hub formed from a ring of interconnected hub elements. FIG. 7(b) depicts the hub in an expanded configuration. FIG. 7(c) depicts the hub in a constrained configuration. FIG. 7(d) depicts a device having a hub formed from two joined rings of interconnected hub elements.

DETAILED DESCRIPTION

Figure 1A:
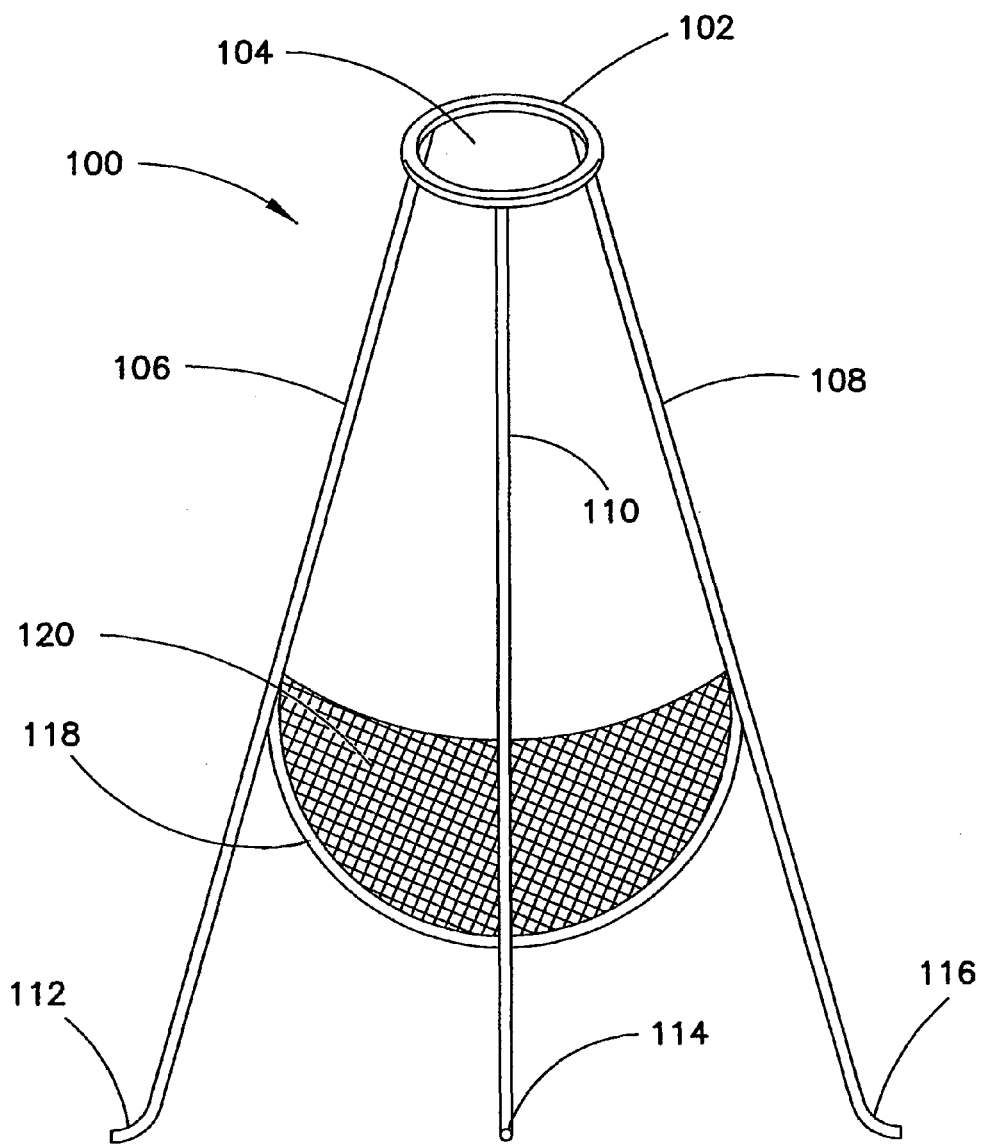
FIG. 1(a) depicts a schematic view of one embodiment of a device of the invention.

Definitions:

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can be used in the practice or testing of the invention. The materials, methods, and examples disclosed herein are illustrative only and not intended to be limiting.

The terms "proximal" and "distal" are used to denote a direction or position relative to each other. Unless otherwise indicated, the recitation of "proximal" or "distal" portions of a frame does not refer to any particular orientation of the implantable frame within a body. The devices described herein can be used in many different body lumens, including the arterial system, venous system, biliary ducts, ureteral passages and alimentary canal and can be implanted in any suitable orientation within the body.

The term "implantable" refers to an ability of a device to be positioned at a location within a body, such as within a body vessel. Furthermore, the terms "implantation" and "implanted" refer to the positioning of a device at a location within a body, such as within a body vessel.

The term "biocompatible material" refers to a material that is compatible with living tissue or a living system by not being toxic or injurious and not causing immunological rejection.

The term "biodegradable material" refers to a material that dissipates upon implantation within a body, independent of the mechanisms by which dissipation can occur, such as dissolution, degradation, absorption and excretion. The actual choice of which type of materials to use may readily be made by one of ordinary skill in the art. Such materials are often referred to by different terms in the art, such as "bioresorbable," "bioabsorbable," or "biodegradable," depending upon the mechanism by which the material dissipates. The prefix "bio" indicates that the erosion occurs under physiological conditions, as opposed to other erosion processes, caused for example, by high temperature, strong acids or bases, UV light or weather conditions.

The term "carrier material" refers to a material that forms a mixture with a bioactive agent on a surface or in an implantable medical device. The carrier material may control the release of the bioactive agent from the medical device.

The term "barrier layer" is any layer that is placed over at least a portion of a bioactive agent present in or on an implantable medical device. In general, the bioactive agent will not be present in the barrier layer. Any mixing of a bioactive agent with the barrier layer is unintentional and merely incidental. The barrier layer may or may not be the outer-most layer present on the device. For example, a bioactive agent may be coated onto a surface of a device, a first barrier layer placed over the bioactive agent and further barrier layers and layers containing the same or a different bioactive agent placed on the first barrier layer. The barrier layer may control the release of the bioactive agent from the medical device upon implantation.

The term "controlled release" refers to the release of an agent at a predetermined rate. A controlled release may be constant or vary with time. A controlled release may be characterized by a drug elution profile, which shows the measured rate that the agent is removed from a device in a given solvent environment as a function of time. For example, a controlled release elution profile from a valve may include an initial burst release associated with the deployment of the valve prosthesis, followed by a more gradual subsequent release. A controlled release may be a gradient release in which the concentration of the agent released varies over time or a steady state release in which the agent is released in equal amounts over a certain period of time (with or without an initial burst release).

As used herein, the term "bioactive agent" refers to any pharmaceutically active agent that produces an intended therapeutic effect on the body to treat or prevent conditions or diseases.

As used herein, the term "venous valve-related condition" is any condition presenting symptoms that can be diagnostically associated with improper function of one or more venous valves. In mammalian veins, venous valves are positioned along the length of the vessel in the form of leaflets disposed annularly along the inside wall of the vein which open to permit blood flow toward the heart and close to prevent back flow. Two examples of venous valve-related conditions are chronic venous insufficiency and varicose veins. Chronic venous insufficiency can occur, for example, in the superficial venous system, such as the saphenous veins in the leg, or in the deep venous system, such as the femoral and popliteal veins extending along the back of the knee to the groin.

Valve Prostheses

For the purposes of promoting an understanding of the principles of the invention, reference will now be made to the embodiments illustrated in the drawings and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

Devices and systems of the invention are desirably adapted for deployment within a body lumen, and in particular embodiments, devices and systems of the invention are adapted for deployment within the venous system. Accordingly, preferred devices adapted are venous valves, for example, for percutaneous implantation within veins of the legs or feet to treat venous insufficiency. However, devices and systems of the invention may be adapted for deployment within any tube-shaped body passage lumen that conducts fluid, including but not limited to blood vessels such as those of the human vasculature system, biliary ducts, ureteral passages, respiratory system or the alimentary canal.

In one aspect of the present invention, the implantable device is a self-expanding valve prosthesis for deployment within a bodily passageway, such as a vessel or duct of a patient. The prosthesis includes a frame and at least one leaflet and is typically delivered and implanted using well-known transcatheter techniques for self-expanding or otherwise expandable prostheses. The frame accommodates dynamic variation in the size of the passageway. The valve prosthesis is positioned so as to allow antegrade fluid flow and to restrict retrograde fluid flow. Antegrade fluid flow travels from the distal (upstream) end of the prosthesis to the proximal (downstream) end of the valve, the latter being located closest to the heart in an artificial venous valve when placed within the lower extremities of a patient. Retrograde fluid flow travels from the proximal (downstream) end of the prosthesis to the distal (upstream) end of the valve.

FIG. 1(a) illustrates one embodiment of a device having a frame including hub member 102 positioned at the proximal end of the device. Hub member 102 includes a closed frame defining an aperture 104. Struts 106, 108 and 110 each have one end attached to hub member 102. Struts 106, 108 and 110 are spring-biased to diverge distally from the hub member and contact the vessel wall upon deployment of the device. In one embodiment, the distal ends of struts 106, 108 and 110 terminate at anchoring mechanisms 112, 114 and 116 respectively. Such anchoring mechanisms, which are adapted to engage a wall of the body vessel when the device is deployed, are known to those skilled in the art and include, but are not limited to, hooks, barb and adhesives. Upon deployment within a vessel, anchoring mechanisms 112, 114 and 116 engage the vessel wall and position hub member 102 towards the center of the vessel lumen.

In one embodiment, struts 106, 108 and 110 are sufficiently flexible to allow for flexing of the struts in response to changes in the diameter of the vessel caused, for example, by hydrostatic pressure variations within the fluid within the vessel. In one embodiment, such flexibility allows for changes of up to 100% in the average radial separation of the second ends of the struts relative to the narrowest average radial separation of the second ends of the struts. In other embodiments, such flexibility allows for changes of up to 90%, 80%, 70%, 60%, 50%, 40%, 30%, 20% or 10% in the average radial separation of the second ends of the struts relative to the narrowest average radial separation of the second ends of the struts.

Frame member 118 attaches to struts 106 and 108 and extends to contact strut 110 to provide for the attachment of leaflet 120. In one embodiment, frame member 118 is also attached to strut 110. In another embodiment frame member 118 extends around strut 110 but is not attached to strut 110. In one embodiment, frame member 118 also extends distally from the points of attachment to struts 106 and 108.

In one embodiment, frame member 118 provides support for leaflet 120 and acts to impart an appropriate shape to leaflet 120. In such embodiments, frame element 118 holds the attached portion of the perimeter of the leaflet against the wall of the vessel. In other embodiments, frame member 118 is formed from a material that may not provide such support. In such embodiments, the portion of the perimeter of leaflet 120 attached to frame member 118 may include barbs, hooks, adhesive or other means of attachment. Such attachment means are attached to the vessel wall during or after deployment of the device, for example by using a balloon to push the attachment means against the vessel wall.

Figure 1B:
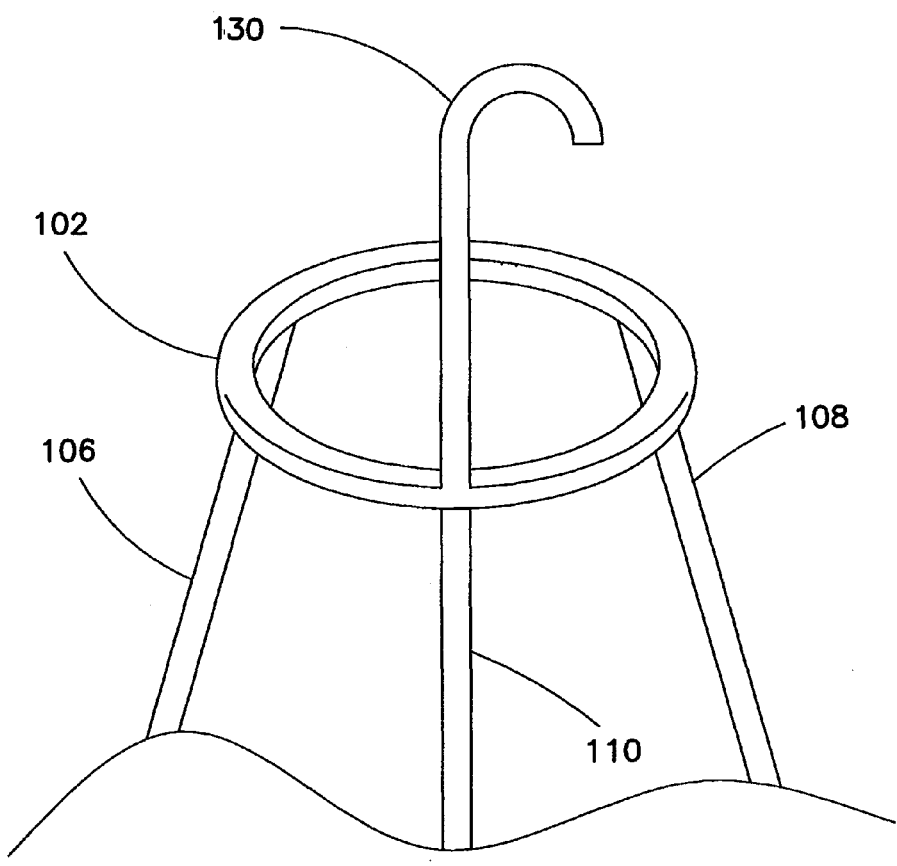
FIG. 1(b) depicts a partial schematic view of another embodiment of a device of the invention.

FIG. 1(b) depicts a partial view of an embodiment having hook 130 attached to hub member 102. Hook 130 can be used to assist in the positioning of the device and, if necessary, in retrieving the device, or part of the device, from the vessel.

Figure 3A:
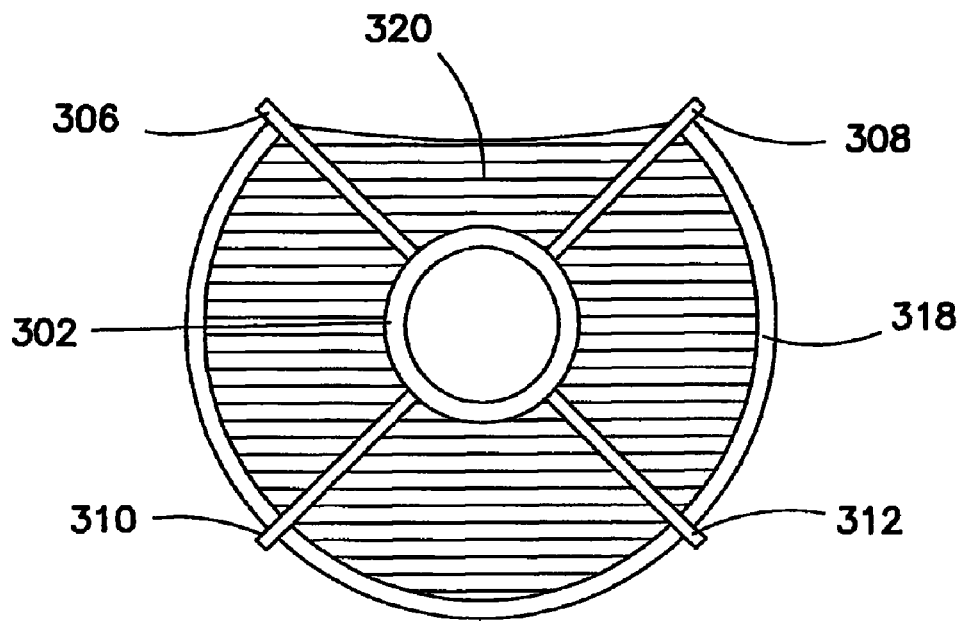
FIGS. 3(a) and 3(b) depict plan views of other embodiments of devices.

The invention also includes devices having four, five, six or more struts. The struts can be the same length or can be of differing lengths. For example, FIG. 3(a) depicts a device having four struts 306, 308, 310 and 312. The ends of frame member 318 are attached to struts 306 and 308. Frame member 318 extends to contact struts 310 and 312. Again, frame member 318 may or may not be attached to struts 310 and 312.

Figure 3B:
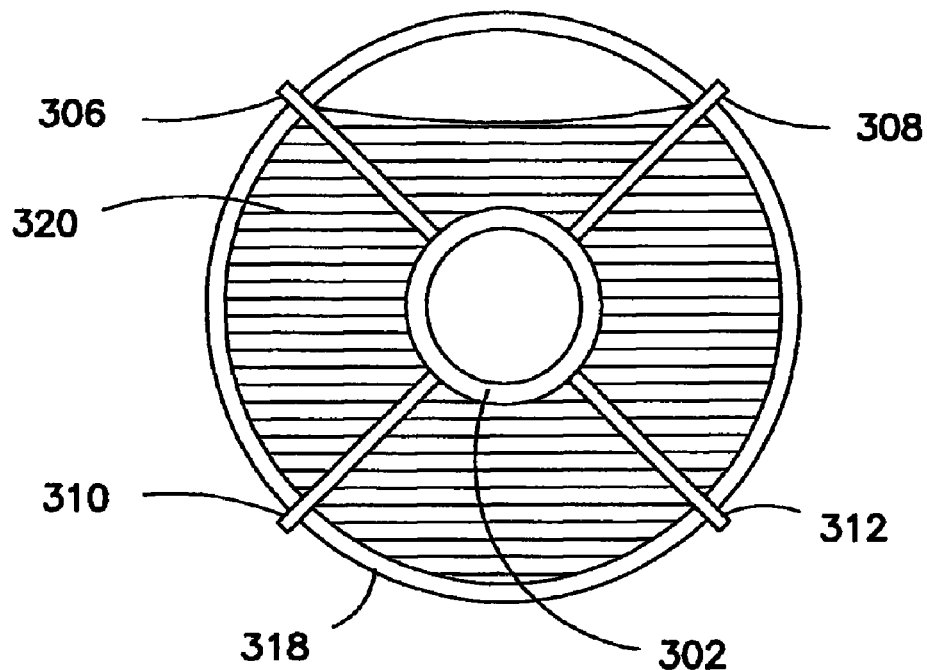

Referring now to FIG. 3(b), in this embodiment, frame member 318 extends around struts 306, 308, 310 and 312 to form a closed frame. Frame member 318 is attached to struts 306 and 308 and may or may not be attached to struts 310 and 312.

In one embodiment, hub member 302 is shaped to provide a circular aperture through the hub member. The aperture provides a path for fluid flow during periods of antegrade flow through the device. It is believed, but not relied upon for the purposes of the invention, that by providing such a flow path, the presence of the aperture at least reduces the incidence of thrombus formation due to pooling and stagnation that can occur in blood vessels when blood is diverted by a solid hub member. The aperture can be any shape that provides for this function. For example, FIGS. 3(a) and 3(b) depict a hub member having an oval shaped aperture. In other embodiments, the hub members have apertures with other shapes, including, but not limited to, square, rectangular, triangular and irregular shaped apertures.

In still other embodiments, the hub member does not include an aperture. In such embodiments, the hub can be formed by the joining of the struts at the proximal end of the device by, for example, soldering or gluing the proximal ends of struts. The struts can also be attached to a hub body as is illustrated in U.S. Publication No. 2002/0193828, published Dec. 19, 2002, the contents of which are incorporated by reference.

Figure 2A:
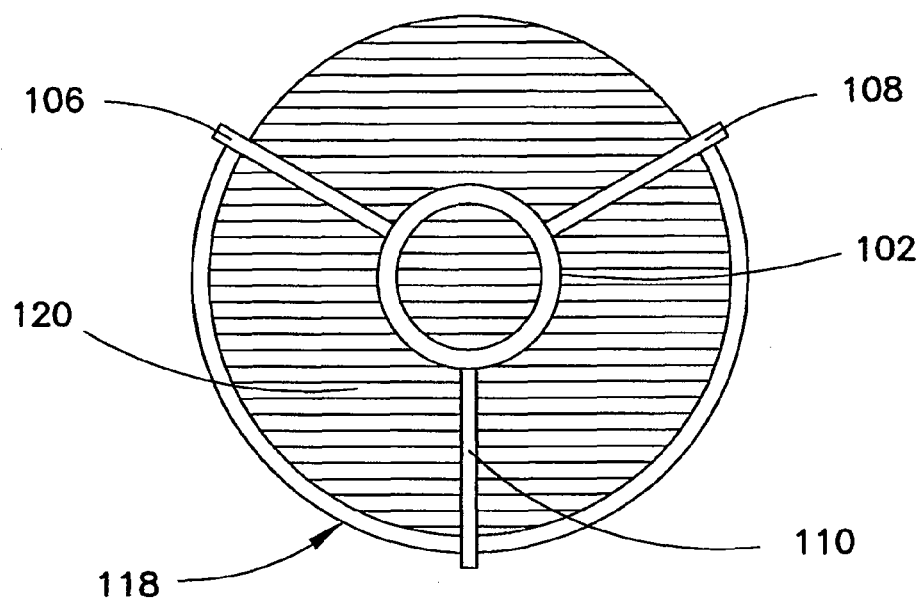
FIGS. 2(a) and 2(b) depict a plan view of one embodiment of a device.
Figure 2B:
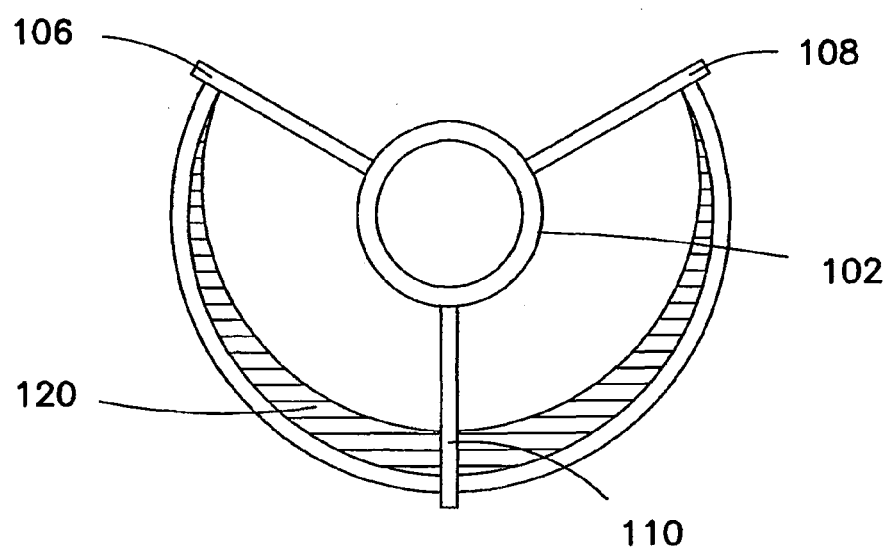

Referring again to FIG. 1, leaflet 120 attaches to frame member 118 and is deformable, in response to fluid flow within the vessel, between a first position allowing fluid flow in an antegrade direction and a second position restricting fluid flow in a retrograde direction. In certain embodiments, frame member 118 extends distally from the points of attachment to struts 106 and 108 to provide a valve pocket formed by the vessel wall and one surface of leaflet 120. Fluid flow in a retrograde direction results in fluid flowing into the valve pocket. Such fluid flow acts to expand the valve pocket and to move leaflet 120 across the vessel lumen to restrict retrograde flow. In contrast, fluid flow in an antegrade direction results in fluid being pushed out of the valve pocket. Leaflet 120 moves toward the vessel wall, collapsing the valve pocket, and allowing fluid flow in an antegrade direction. FIG. 2(a) depicts a plan view from the proximal end of device 100 and shows leaflet 120 positioned to restrict fluid flow in a retrograde direction. FIG. 2(b) depicts a similar view but having leaflet positioned to allow fluid flow in an antegrade direction.

Figure 4A:
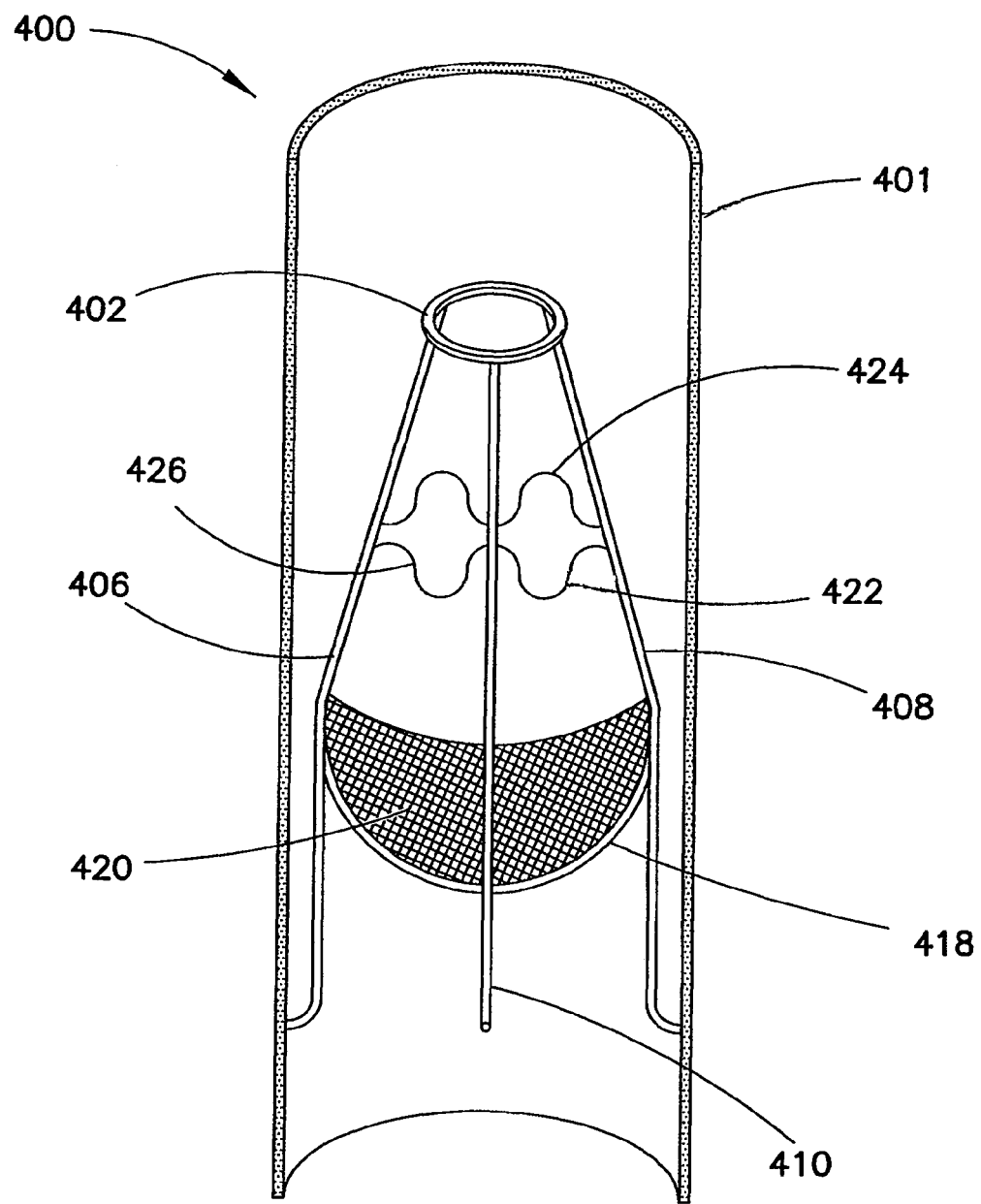
FIGS. 4(a) and 4(b) depict a schematic view of another embodiment of an implantable device.
Figure 4B:
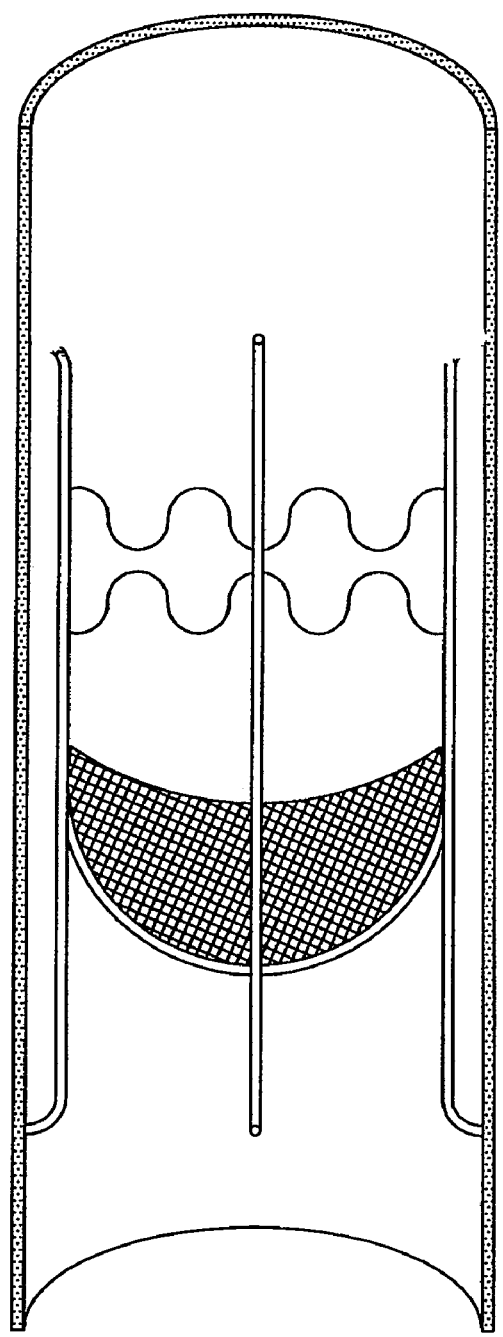

FIGS. 4(a) and 4(b) depict another embodiment of the invention. Again, a device having three struts is depicted. Of course, devices having additional struts are also encompassed. Device 400 includes a hub member 402 that is either biodegradable or can be removed from the remainder of the device during or at some time after implantation of the device. Removal or biodegradation of hub member 402 results in the proximal ends of struts 406, 408 and 410 being released from the hub member. In one embodiment, at least one expanding member connects two of the struts. For example, FIG. 4(a) depicts expanding members 422, 424 and 426 connecting struts 408 and 410, 406 and 408, and 406 and 410 respectively. In FIG. 4(a), hub member 402 remains in place. FIG. 4(b) depicts the same device after hub member 402 either degrades or is otherwise removed. Upon removal of hub member 402, expanding members 422, 424 and 426 expand to push struts 406, 408 and 410 towards the wall of vessel 401. Struts 406, 408 and 410 are held in place by expanding members 422, 424 and 426 and, in certain embodiments, by anchoring mechanisms attached to the distal ends and/or the proximal ends of the struts. Although the struts are moved towards the vessel wall, frame member 418 and attached leaflet 420 remain in position to restrict retrograde flow within the vessel.

Those embodiments in which the hub member is biodegradable or removable may include an aperture though the hub member to allow fluid flow during periods of antegrade flow. However, the present invention also includes embodiments in which a biodegradable or removable hub member does not include an aperture. Elimination of the hub member upon implantation, or soon after implantation, removes restriction to fluid flow that may lead to thrombus formation.

Figure 5:
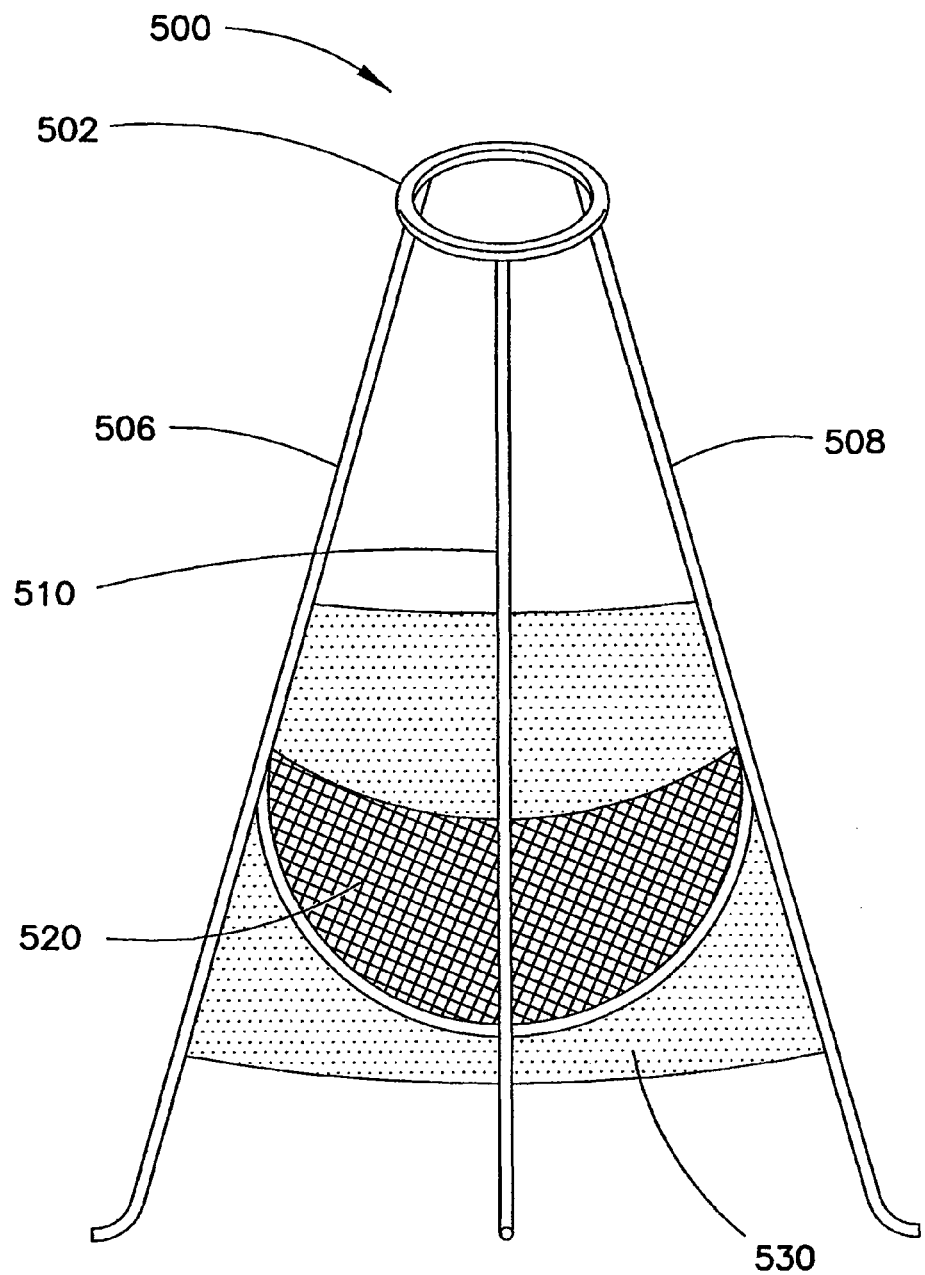
FIG. 5 depicts a schematic view of another embodiment of the device.

FIG. 5 depicts another embodiment. A device having three struts is depicted, but devices having additional struts are also encompassed. As in previous embodiments, struts 506, 508 and 510 diverge distally from hub member 502. However, in this embodiment, graft sheet 530 is attached to struts 506 and 508 and extends between these struts. FIG. 5 depicts leaflet 520 attached to graft sheet 530 and also directly to struts 506 and 508. In other embodiments, leaflet 520 is attached to graft sheet 530 but is not directly attached to the struts. The graft sheet disclosed above and depicted in FIG. 5 may replace the frame member as a means of supporting the leaflet in any of the previously disclosed embodiments, such as those depicted in FIGS. 1 to 4.

Figure 6:
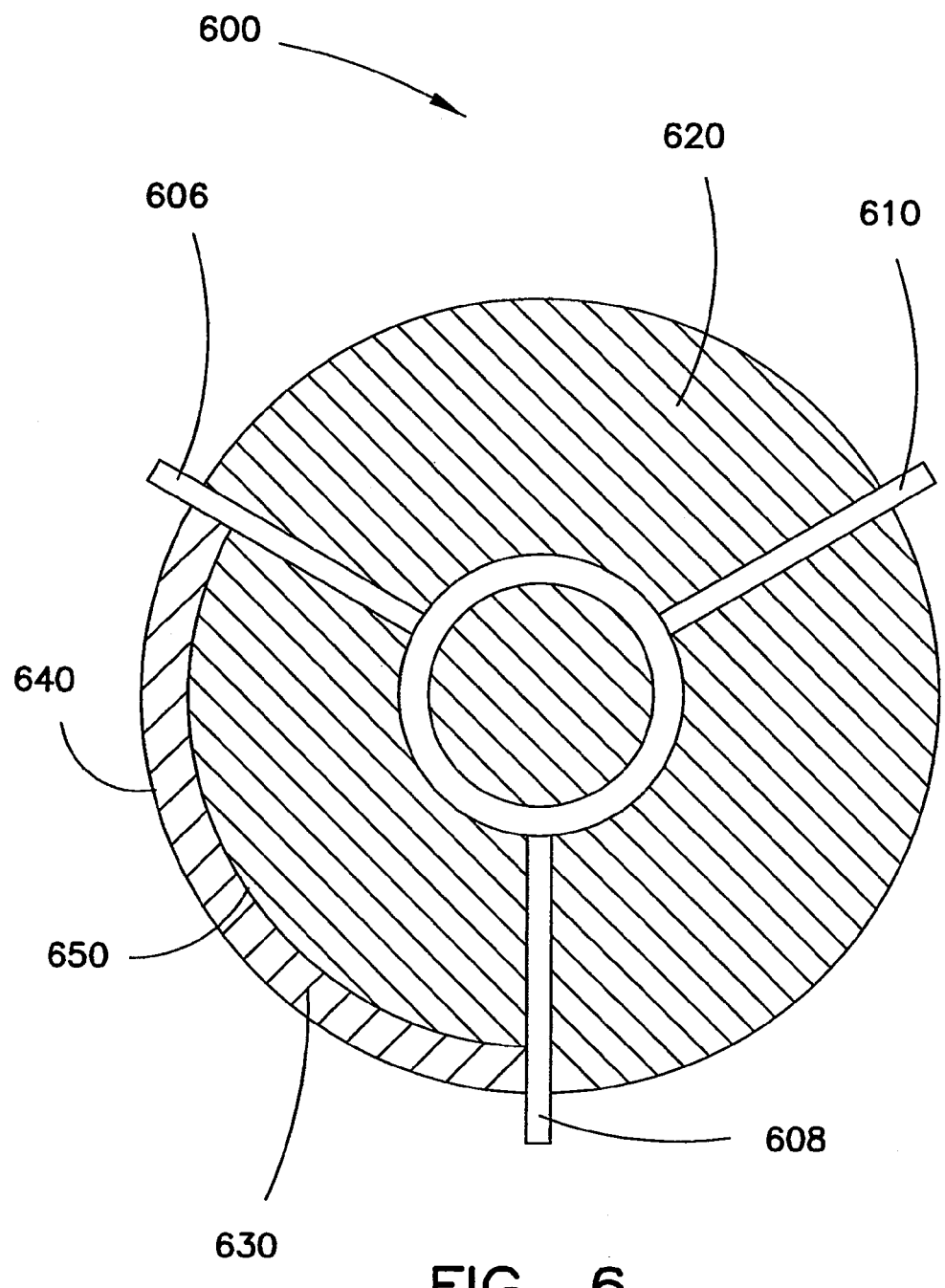
FIG. 6 depicts a schematic view of yet another embodiment of the device.

FIG. 6 depicts an embodiment in which graft sheet 630 is supported by two support members 640 and 650. Support members 640 and 650 extend between struts 606 and 608 and are shaped to position graft sheet 630 against the vessel wall when the device is in the expanded configuration. By positioning graft sheet 630 so, support members 640 and 650 help to ensure that retrograde flow is restricted when leaflet 620 is positioned across the vessel lumen. The invention includes embodiments in which graft sheet 630 in supported by one, two, three, four or more support members.

Figure 8A:
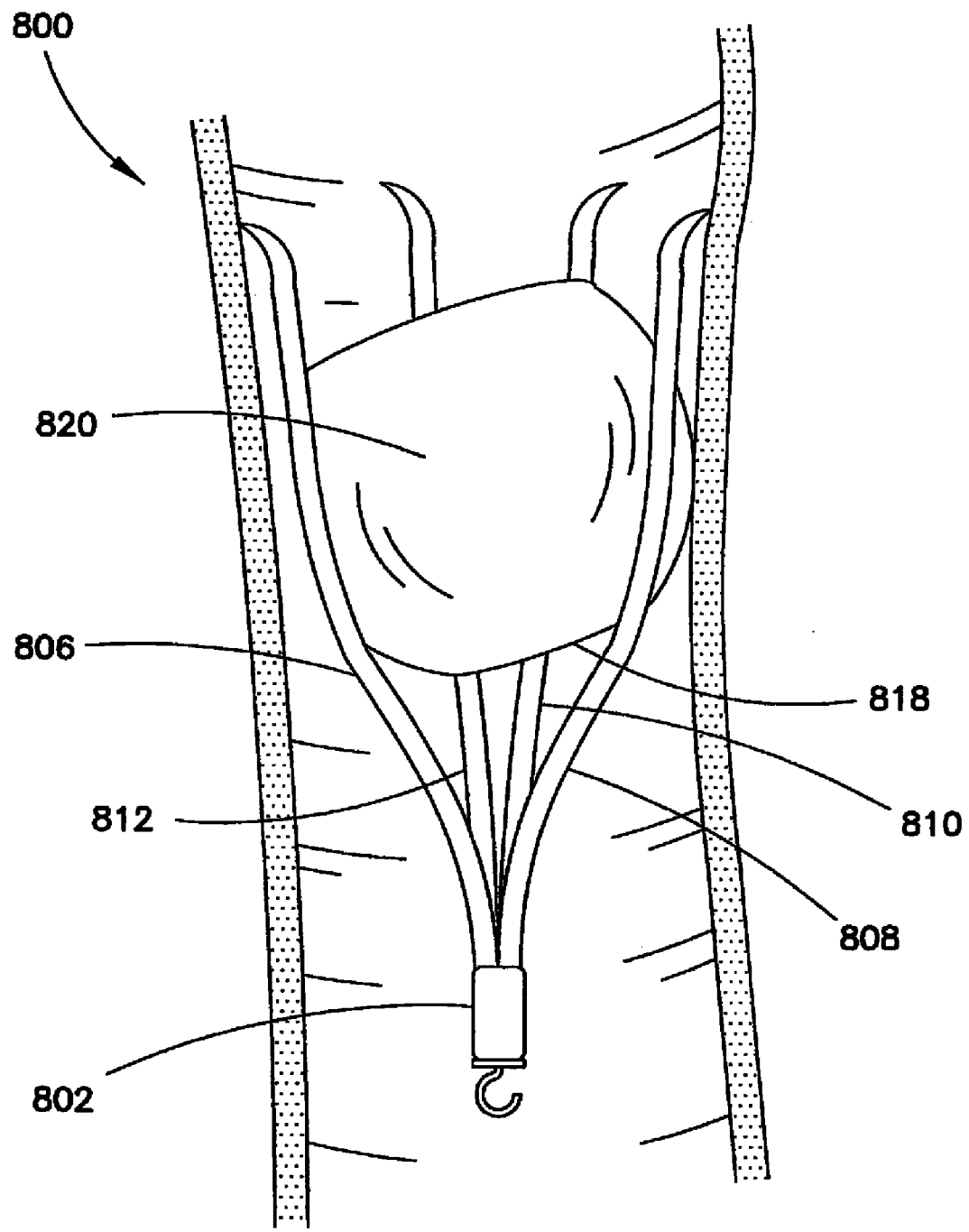
FIGS. 8(a)-(c) depict schematic views of another embodiment of the device.
Figure 8B:
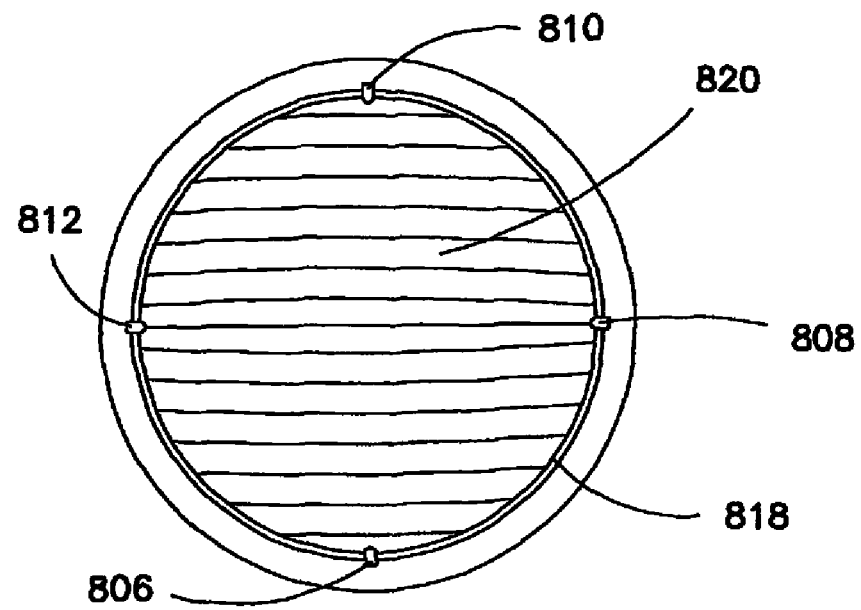
Figure 8C:
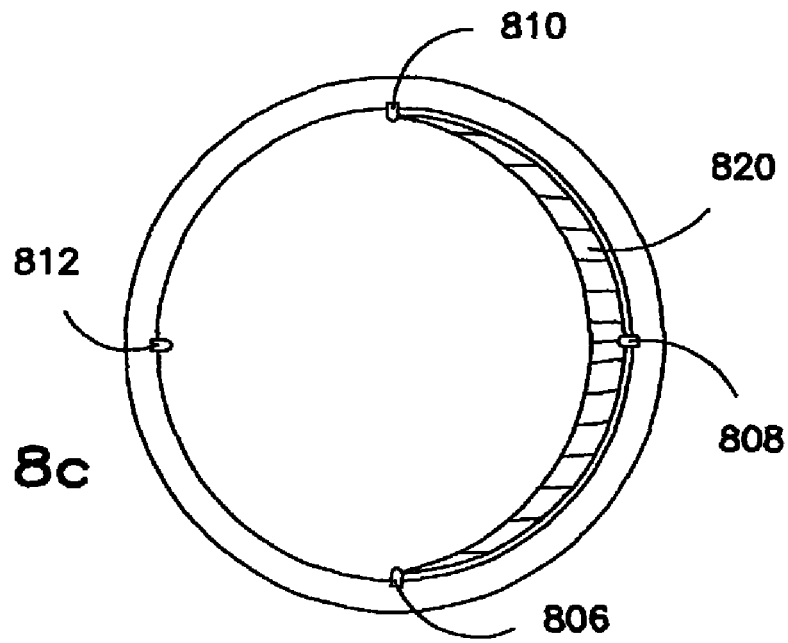

In other embodiments, the leaflet is attached to the frame in a configuration such that the hub member is positioned at the distal end of the device when the device is positioned within a body passage so as to allow flow in an antegrade direction and restrict flow in a retrograde direction. FIGS. 8(a), 8(b) and 8(c) illustrate one such embodiment. In FIG. 8(a), the frame includes struts 806, 808, 810 and 812, one end of each of which are joined at hub member 802. Struts 806, 808, 810 and 812 are spring-biased to diverge proximally from hub member 802 and contact the vessel wall upon deployment of the device. In this embodiment, hub member 802 does not include an aperture. However, embodiments including a hub member with an aperture positioned at the distal end of the device are also contemplated.

Frame member 818 attaches to struts 806 and 810 and extends to contact strut 808 to provide for the attachment of leaflet 820. In one embodiment, frame member 808 is also attached to strut 808. In another embodiment frame member 818 extends around strut 808 but is not attached. In one embodiment, frame member 808 also extends distally from the points of attachment to struts 806 and 810. As in the embodiment illustrated in FIG. 1, frame member 818 can hold the attached portion of the perimeter of leaflet 820 against the wall of the vessel. In other embodiments, the portion of the perimeter of leaflet 820 attached to frame member 818 may include barbs, hooks, adhesive or other means of attachment.

Leaflet 820 is deformable, in response to fluid flow within the vessel, between a first position allowing fluid flow in an antegrade direction and a second position restricting fluid flow in a retrograde direction. FIG. 8(b) shows the device viewed from the proximal end and illustrates leaflet 820 positioned to restrict flow in an retrograde direction. FIG. 8(c) shows a similar view illustrating leaflet 820 positioned to allow flow in an antegrade direction.

Figure 9A:
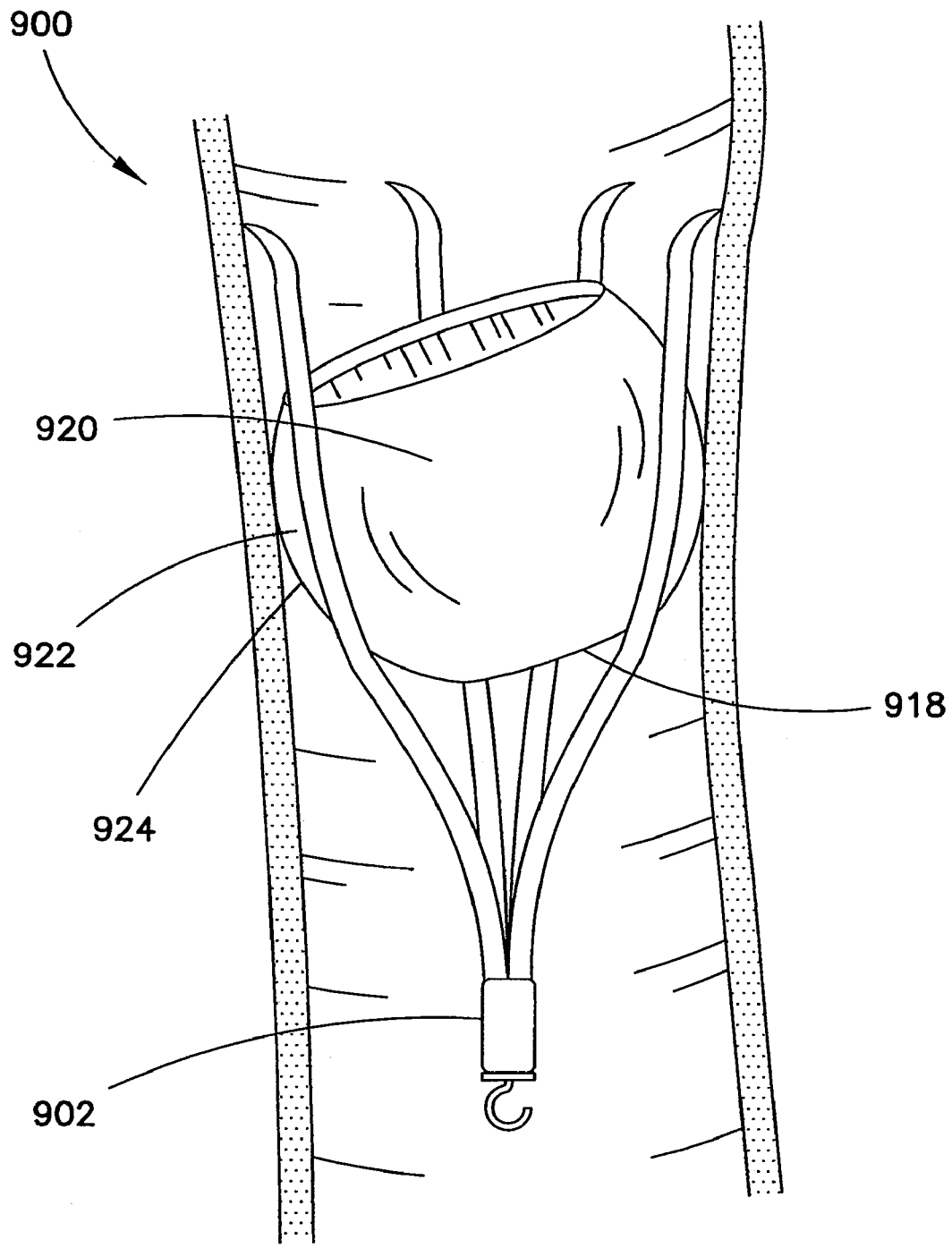
FIGS. 9(a)-(c) depict schematic views of yet another embodiment of the device.
Figure 9B:
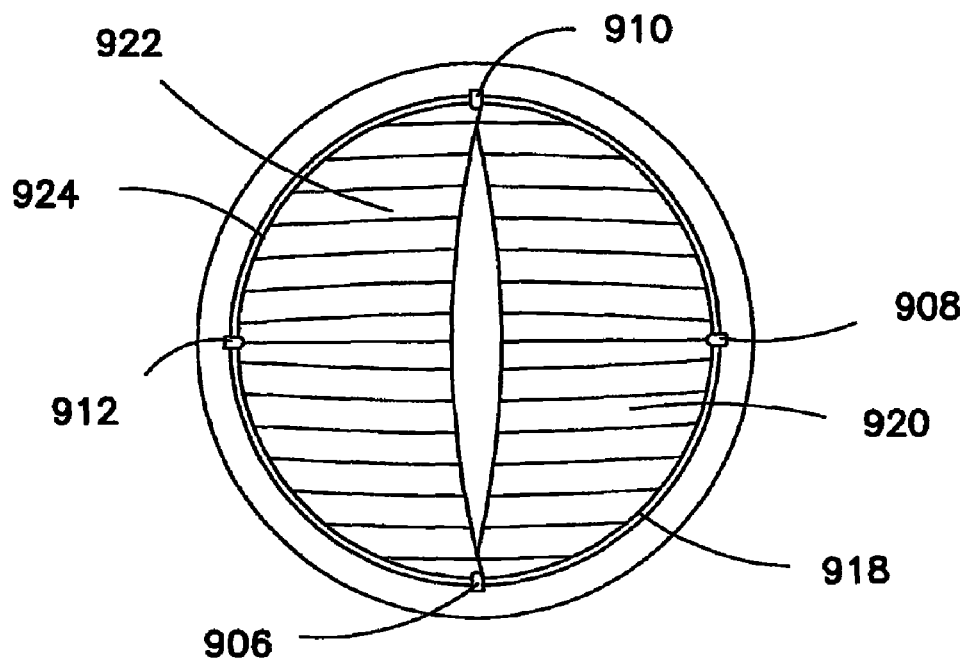
Figure 9C:
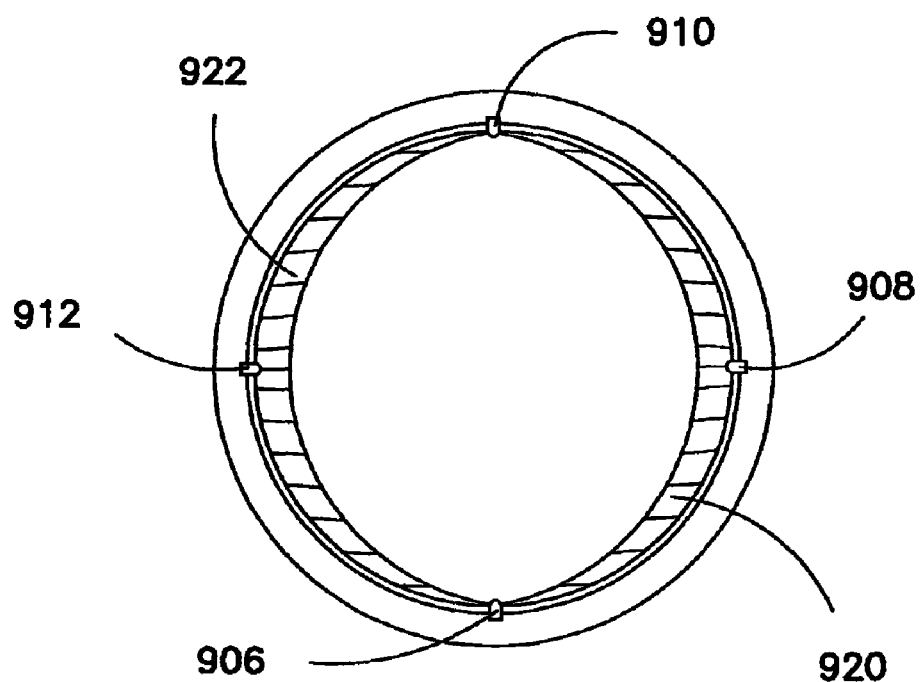

In yet other embodiments, two or more leaflets are attached to the frame. FIGS. 9(a), 9(b) and 9(c) illustrate one such embodiment. In FIG. 9(a), the frame includes struts 906, 908, 910 and 912, one end of each of which are joined at hub member 902. The struts are spring-biased to diverge proximally from hub member 902 and contact the vessel wall upon deployment of the device.

Frame member 918 attaches to struts 906 and 910 and extends to contact strut 908 to provide for the attachment of leaflet 920. In one embodiment, frame member 908 is also attached to strut 908. In another embodiment frame member 918 extends around strut 908 but is not attached. In one embodiment, frame member 908 also extends distally from the points of attachment to struts 906 and 910. Frame member 924 provides similar means of attachment for leaflet 922.

Leaflets 920 and 924 are deformable, in response to fluid flow within the vessel, between a first position allowing fluid flow in an antegrade direction and a second position restricting fluid flow in a retrograde direction. FIG. 9(b) shows the device viewed from the proximal end and illustrates leaflets 920 and 924 positioned to restrict flow in an retrograde direction. FIG. 9(c) shows a similar view illustrating leaflets 920 and 924 positioned to allow flow in an antegrade direction.

Frame Composition and Manufacture

The materials used in the manufacture of the device frame elements such as the struts, hub member, support members and/or frame members can be selected from a well-known list of suitable metals and polymeric materials. Preferred materials include those materials that can provide the desired functional characteristics with respect to mechanical load bearing, biological compatibility, modulus of elasticity, radio-opacity, or other desired properties. For some embodiments, the materials used to form these elements of the device can comprise a material that exhibits excellent corrosion resistance. For some embodiments, the material can be selected to be sufficiently radiopaque and create minimal artifacts during magnetic resonance imaging techniques (MRI). In other embodiments, these elements can comprise a metal, a metal alloy, a polymer, or any suitable combination thereof, for example a multiple layered element.

In various embodiments, the frame includes a metallic material selected from stainless steel, nickel, silver, platinum, palladium, gold, titanium, tantalum, iridium, tungsten, a nickel-titanium alloy, a superelastic nickel-titanium (NiTi) alloy sold under the trade name NITINOL® or inconel. Other materials suitable for use in the frame are described in U.S. Publication No. 2007/0038295A1, published Feb. 15, 2007, the contents of which are incorporated by reference.

One important characteristic of the frame is the ability to be compressed to allow for delivery within the lumen of a delivery catheter. In certain embodiments, the diameter of the hub member is such that it can be placed within the delivery catheter without compression. In other embodiments, the hub member may be compressed to allow for delivery.

In one embodiment, the frame can include materials, such as stainless steel, that may be bent into a constrained configuration suitable for placement within a delivery catheter, and which, when the constraint is released, will spring back to an unconstrained configuration. If necessary, fillets may be placed at appropriate regions of the device to reduce bending stresses.

In another embodiment, the frame can include a self-expanding material, such as the superelastic NiTi alloy NITINOL. NITINOL is a self-expanding material that can be deformed by collapsing the device and creating stress which causes the NiTi to reversibly change to the martensitic phase. The device can be restrained in the deformed condition inside a delivery catheter to facilitate the insertion into a patient's body, with such deformation causing the isothermal phase transformation. Once within the body lumen, the restraint on the device can be removed, thereby reducing the stress thereon so that the superelastic valve frame returns towards its original undeformed shape through isothermal transformation back to the austenitic phase. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," Scientific American, 281: 74-82 (November 1979).

Other suitable materials used in the frame include carbon or carbon fiber, cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, polylactic acid, polyglycolic acid, a polyanhydride, polycaprolactone, polyhydroxybutyrate valerate, a biodegradable polymeric material, a biocompatible polymeric material, a protein, an extracellular matrix component, collagen, chitin, fibrin, another biologic agent, or mixtures or copolymers of these materials.

As mentioned above, in certain embodiments, biodegradable materials have particular application in the manufacture of the hub member. Such biodegradable materials include, but are not necessarily limited to, polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, poly-alpha-hydroxy acids, trimethlyene carbonate, poly-beta-hydroxy acids, polyorganophosphazines, polyanhydrides, polyesteramides, polyethylene oxide, polyester-ethers, polyphosphoester, polyphosphoester urethane, cyanoacrylates, poly(trimethylene carbonate), poly(iminocarbonate), polyalkylene oxalates, polyvinylpyrolidone, polyvinyl alcohol, poly-N-(2-hydroxypropyl)-methacrylamide, polyglycols, aliphatic polyesters, poly(orthoesters), poly(ester-amides), polyanhydrides, modified polysaccharides and modified proteins.

Some specific examples of bioabsorbable materials include polymers and co-polymers comprising a polylactic acid, a polyglycolic acid, a polycaprolactone or derivatives thereof. Suitable bioabsorbable materials for a frame include: poly(epsilon-caprolactone), poly(dimethyl glycolic acid), poly(hydroxy butyrate), poly(p-dioxanone), polydioxanone, PEO/PLA, PLA, poly(lactide-co-glycolide), poly(hydroxybutyrate-co-valerate), poly(glycolic acid-co-trimethylene carbonate), poly(epsilon-caprolactone-co-p-dioxanone), poly-L-glutamic acid or poly-L-lysine, polylactic acid, polylactide, polyglycolic acid, polyglycolide, poly(D,L-lactic acid), L-polylactic acid, poly(glycolic acid), polyhydroxyvalerate, cellulose, chitin, dextran, fibrin, casein, fibrinogen, starch, collagen, hyaluronic acid, hydroxyethyl starch, and gelatin. The hub member can also include one or more naturally derived bioabsorbable polymers, including modified polysaccharides such as cellulose, chitin, and dextran or modified proteins such as fibrin and casein.

In some embodiments, the hub member or a portion of the hub member can include one or more metallic bioabsorbable materials. Suitable metallic bioabsorbable materials include magnesium, titanium, zirconium, niobium, tantalum, zinc and silicon and mixtures and alloys. For example, a zinc-titanium alloy such as discussed in U.S. Pat. No. 6,287,332, which is incorporated herein by reference, can be used. The metallic bioabsorbable material can further contain lithium, sodium, potassium, calcium, iron and manganese or mixtures thereof. For example, an alloy containing lithium and magnesium or sodium and magnesium can be used. The physical properties of the hub member can be controlled by the selection of the metallic bioabsorbable material, or by forming alloys of two or more metallic bioabsorbable materials. For example, when 0.1% to 1%, percentage by weight, titanium is added to zinc, the brittle quality of crystalline zinc can be reduced. In another embodiment, when 0.1% to 2%, percentage by weight, gold is added to a zinc-titanium alloy, the grain size of the material is reduced upon cures and further the tensile strength of the material increases.

The frame can be fabricated using any suitable method known in the art. For example, the frame can be formed from a solid wire. In certain embodiments, the frame member and or the support members are manufactured from a narrower gage wire than the struts.

In those embodiments including expanding members, these members can be formed from the same materials mentioned above as suitable for the other components of the frame. The expanding members can include a "V" shaped or arched structure (or a compressed spring-like structure) that is maintained in a compressed state by the hub member when the device is in the deployed configuration. When the hub member is removed, either by degrading or by physical removal, compression is released and the proximal ends of the struts are pushed apart and towards the vessel wall by expansion of the expanding members.

The device can be formed into the required shape by bending or by forming joins at the appropriate positions. Components of the frame can be joined by any method known in the art, including soldering, welding or adhesion. In certain embodiments, two or more components of the frame are manufactured from a single piece of material, for example, by process such as laser cutting, waterjet cutting or photochemical etching.

In certain embodiments, the length of the deployed device, measured along a longitudinal axis from the distal end to the proximal end, is preferably between 5 mm and 50 mm or higher, including 5, 6, 7, 8, 9, 10, 11, 12, 13, 14, 15, 16, 17, 18, 19, 20, 21, 22, 23, 24, 25, 26, 27, 28, 29, 30, 30, 32, 34, 35, 36, 38, 40, 42, 44, 45, 46, 48 and 50 mm, and any increment of 0.25 mm or 0.10 mm increment thereof. Some preferred embodiments have lengths of 8, 12, 13, 16, 20, 23, 24, 25, 28, 32 or 33 mm.

Typical devices may have a compressed external diameter of between about 2 millimeters and about 3, 4, 5 or 6 millimeters for delivery and an expanded external diameter in a body lumen of between about 3 millimeters and about 5, 7, 10, 12, 15, 17 or 20 millimeters when released from compression in a body vessel.

Figure 7A:
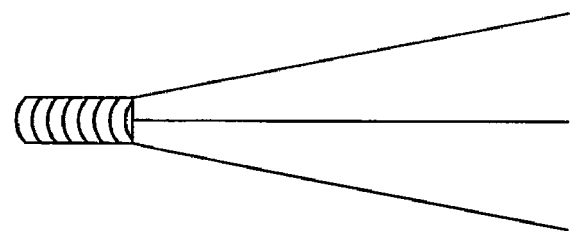
FIGS. 7(a)-(d) depict schematic views of other embodiments of devices.
Figure 7B:
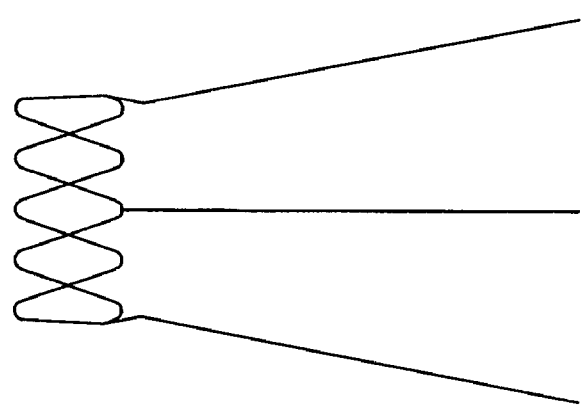
Figure 7C:
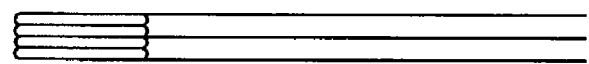
Figure 7D:
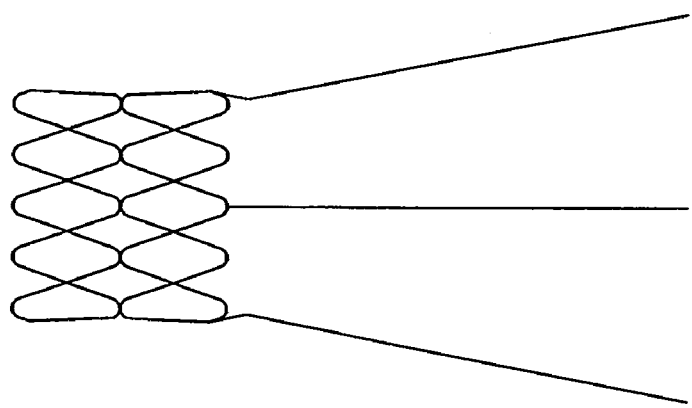

FIGS. 7(a)-(d) show exemplary embodiments including hubs having an aperture that are suitable for use in the present devices. The devices are shown as having three struts. Of course, such devices having four, five of more struts are also contemplated. In FIG. 7(a), the hub formed from a cannula of an external diameter small enough to fit inside a delivery device. In FIGS. 7(b) and 7(c), the hub is expandable and is formed from a ring of interconnected hub elements. The hub elements form a "V" shaped or arched structure (a spring-like structure) that is maintained in a compressed state by the delivery system until the device is deployed. FIG. 7(b) depicts the hub elements in an expanded configuration. FIG. 7(c) depicts a constrained configuration. FIG. 7(d) depicts a device having a hub formed from two joined rings of interconnected hub elements. Many other expandable structures are known to those skilled in the art and are encompassed in the present embodiments.

Graft Sheet and Leaflet Composition and Manufacture

The graft sheet and leaflet can manufactured from a wide variety of natural or synthetic materials. In one embodiment, the leaflet is formed from the same material as is the graft sheet. In another embodiment, the leaflet is formed from a material that is different from the material forming the graft sheet.

In one embodiment, the leaflet is formed from a mammalian tissue valve, for example a porcine leaflet. In one embodiment, such leaflets have a parabolic shape that may be attached to the graft sheet or frame member to provide a parabolic-shaped leaflet. The graft sheet may also be formed from mammalian tissue. In one embodiment, the graft sheet is formed from porcine tissue.

After harvesting, such graft sheet and leaflet material may chemically fixed by cross-linking. Such treatment methods are known to those practicing the art and include, but are not limited to, chemical fixation using aldehydes, such as formaldehyde or glutaraldehyde. Prior to chemical fixing, these materials may be treated to remove cellular components. Examples of such decellularization treatments are disclosed in U.S. Pat. No. 5,595,571, the contents of which are incorporated by this reference. In addition, various other treatment techniques may be used to mitigate problems caused by the calcification of chemically-fixed material. Examples of such techniques are disclosed in U.S. Pat. Nos. 4,553,974 and 6,547,827, the contents of which are incorporated by reference.

In certain embodiments, the graft sheet and/or the leaflet may be formed from material from a human or non-human primate origin. In certain embodiments, the graft sheet and/or the leaflet are comprised of a naturally derived or synthetic collagenous material, and especially an extracellular matrix material ("ECM material"). Suitable ECM materials include, for instance, submucosa (including, for example, small intestinal submucosa ("SIS"), stomach submucosa, urinary bladder submucosa, or uterine submucosa), renal capsule membrane, dura mater, pericardium, serosa, and peritoneum or basement membrane materials, including liver basement membrane. These layers may be isolated and used as intact natural sheet forms, or reconstituted collagen layers including collagen derived from these materials or other collagenous materials may be used. In certain embodiments, the ECM material is processed so that it retains bioactivity such that it is able to stimulate angiogenesis and cell ingrowth into the collagenous matrix. For additional information as to submucosa materials useful in these embodiments, and their isolation and treatment, reference can be made to U.S. Pat. Nos. 4,902,508, 5,554,389, 5,993,844, 6,206,931, and 6,099,567, the contents of which are incorporated herein by reference. Renal capsule tissue can also be obtained from warm blooded vertebrates, as described more particularly in U.S. Pat. No. 7,087,089 and International Patent Application Serial Number PCT/US02/20499, filed Jun. 28, 2002, and published Jan. 9, 2003 as International Publication Number WO03002165, the contents of which are incorporated herein by reference.

In one embodiment of the invention, the ECM material is porcine SIS. SIS can be prepared according to the method disclosed in U.S. publication number 2004/0180042A1, published Sep. 16, 2004, the contents of which are incorporated herein by reference.

The material used for the manufacture of the graft and/or the valve leaflet may include a biocompatible material, and is, in one embodiment, a bioremodelable material. Suitable biocompatible materials may be made from natural or synthetic polymers, including collagen, cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material such as polytetrafluoroethylene, polylactic acid, polyglycolic acid, a polyanhydride, polycaprolactone, polyhydroxy-butyrate valerate, polyhydroxyalkanoate, a biodegradable polymer, a biocompatible polymer, or mixtures or copolymers of these materials.

In certain embodiments, the material is a biocompatible polyurethane, for example THORALON (THORATEC, Pleasanton, Calif.). THORALON has been used in certain vascular applications and is characterized by thromboresistance, high tensile strength, low water absorption, low critical surface tension, and good flex life. THORALON is believed to be biostable and to be useful in vivo in long term blood contacting applications requiring biostability and leak resistance. Because of its flexibility, THORALON is useful in larger vessels, such as the abdominal aorta, where elasticity and compliance is beneficial.

THORALON is a polyurethane base polymer (referred to as BPS-215) blended with a siloxane containing surface modifying additive (referred to as SMA-300) and is described in U.S. Pat. Nos. 6,939,377 and 4,675,361, which are incorporated herein by reference. A process for synthesizing SMA-300 is described, for example, in U.S. Pat. Nos. 4,861,830 and 4,675,361, which are incorporated herein by reference.

THORALON can be manipulated to provide either porous or non-porous THORALON. Formation of porous and non-porous THORALON is described in U.S. Pat. No. 6,752,826 and U.S. Patent Application Publication Nos. 2003/0149471A1 and 2007/0038295A1, which are incorporated herein by reference.

A variety of other biocompatible polyurethanes may also be employed. These include polyurethane ureas that preferably include a soft segment and include a hard segment formed from a diisocyanate and diamine. For example, polyurethane ureas with soft segments such as polytetramethylene oxide, polyethylene oxide, polypropylene oxide, polycarbonate, polyolefin, polysiloxane (i.e. polydimethylsiloxane), and other polyether soft segments made from higher homologous series of diols may be used. Mixtures of any of the soft segments may also be used. The soft segments also may have either alcohol end groups or amine end groups. The molecular weight of the soft segments may vary from about 500 to about 5,000 g/mole. Examples of the diisocyanate and diamine used as a component of the hard segment are described in U.S. Patent Application Publication No. 200710038295A1, the contents of which are incorporated by reference.

Other biocompatible polymers can include polyurethanes having siloxane segments, also referred to as a siloxane-polyurethane. Examples of polyurethanes containing siloxane segments include polyether siloxane-polyurethanes, polycarbonate siloxane-polyurethanes, and siloxane-polyurethane ureas. Examples of siloxane-polyurethanes are disclosed in U.S. Pat. Application Publication No. 2002/0187288 A1, which is incorporated herein by reference.

In another embodiment of the invention, the graft sheet and/or leaflet is formed from or coated with a polyparaxylene ("parylene") or a parylene derivative, such as parylene C or parylene N. For example, the parylene or parylene derivative is created by first heating p-xylene or a suitable derivative at an appropriate temperature (for example, at about 950° C.) to produce the cyclic dimer di-p-xylylene (or a derivative thereof). The resultant solid can be separated in pure form, then cracked and pyrolyzed at an appropriate temperature (for example, at about 680° C.) to produce a monomer vapor of p-xylylene (or derivative). The monomer vapor can then be cooled to a suitable temperature (for example, below 50° C.) and the graft sheet and/or leaflet formed by vapor phase deposition.

Attachment of the Graft Sheet and Leaflet

The graft sheet may be attached to the struts by any appropriate attachment means, including but not limited to stitching, adhesive, fasteners and tissue welding using heat and/or pressure. Alternatively, the graft sheet may be formed on the struts by an appropriate means, including but not limited to vapor deposition, spraying, electrostsatic deposition, ultrasonic deposition, or dipping. Similar methods may be used to attach the leaflet to the frame and/or the graft sheet. Further details of methods of forming a leaflet and attaching the leaflet to a struts and/or frame member are disclosed in U.S. Publication No. 2007/0093887, published Apr. 26, 2007, which is incorporated herein by reference.

Implantable Devices Including Bioactive Agents

Devices of the present invention can include one or more bioactive agents. Preferably, the bioactive agent is releasably associated with the device, meaning that the bioactive agent can be released from the device upon implantation in the body of a patient. Preferably, the bioactive agent is released in a controlled manner. A bioactive agent can be included in any suitable part of the device frame, graft sheet and/or leaflet. The bioactive agent can be incorporated within the material of and/or coated onto the surface of one or more of these elements. The bioactive agent can also be placed in holes, wells or groves formed in the frame.

Selection of the type of bioactive agent, the portions of the device containing the bioactive agent and the manner of attaching the bioactive agent to the device can be chosen to perform a desired therapeutic function upon implantation and, in particular, to achieve controlled release of the bioactive agent at a desired rate.

A bioactive agent can be coated directly on a device surface as a separate layer. The bioactive agent can be bonded to the surface directly via a covalent bond or via a linker molecule which covalently links the bioactive agent and the surface. The bioactive agent can also be bound to the surface by ionic, hydrophobic or hydrogen bonding interactions.

Alternatively, a bioactive agent can be attached to a device surface within a layer including a carrier material. For example, a bioactive agent can be mixed with the carrier material, such as a polymer, and applied to a surface of the device, for example, by spray or dip coating onto the surface. If the carrier material is biostable, the bioactive agent can be released by diffusion through the carrier material. If the carrier material is biodegradable, the bioactive agent can be released upon erosion of the biodegradable carrier material.

The carrier material may include a biostable polymer, a biodegradable polymer or any combination thereof. In one embodiment, the bioactive agent is blended with a biostable polymer to deposit the bioactive agent within the porous channels within the biostable polymer that permits release of the bioactive agent from the device upon implantation. Alternatively, a blend of the bioactive agent and a bioabsorbable polymer can be incorporated within a biostable polymer matrix to permit dissolution of the bioabsorbable polymer through channels or pores in the biostable polymer matrix upon implantation in the body, accompanied by release of the bioactive agent.

A porous barrier layer can be posited over some, or all, of the bioactive agent to control the release of the bioactive agent from the device. Multiple porous barrier layers and/or the pore size in the porous barrier layer can be used to control the rate of release of the bioactive agent.

One or more bioactive agents may be impregnated into the material of the frame, graft and/or leaflet. Methods of impregnating bioactive agents into the structure of non-metallic medical devices are described in U.S. Pat. No. 5,624,704, which is hereby incorporated by reference. One or more bioactive agents may be impregnated into such devices by contacting the device with the bioactive agent in a suitable solvent. In some cases, a penetrating ingredient is also added.

Bioactive Agents

In one embodiment, the bioactive agent is an antithrombogenic agent. Implantable devices including an antithrombogenic agent are particularly preferred for implantation in areas of the body that contact blood. An antithrombogenic agent is any agent that inhibits or prevents thrombus formation within a body vessel. Types of antithrombotic agents include anticoagulants, antiplatelets, and fibrinolytics. Examples of antithrombotic agents include but are not limited to anticoagulants such as thrombin, Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin.

Further examples of antithrombotic agents include anticoagulants such as heparin, low molecular weight heparin, covalent heparin, synthetic heparin salts, coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CI-1083, JTV-803, razaxaban, BAY 59-7939, and LY-51,7717; antiplatelets such as eftibatide, tirofiban, orbofiban, lotrafiban, abciximab, aspirin, ticlopidine, clopidogrel, cilostazol, dipyradimole; fibrinolytics such as alfimeprase, alteplase, anistreplase, reteplase, lanoteplase, monteplase, tenecteplase, urokinase, streptokinase, or phospholipid encapsulated microbubbles; and other bioactive agents such as endothelial progenitor cells or endothelial cells.

Another example of an antithrombotic agent is a nitric oxide source such as sodium nitroprussiate, nitroglycerin, S-nitroso and N-nitroso compounds. In one embodiment, a material capable of releasing nitric oxide from blood-contacting surfaces can be delivered by the device. Examples of such materials include, but are not limited to, those described in U.S. publication number 200410224868A1, published Nov. 11, 2004, and 2002/0115559A1, published Aug. 22, 2002, the contents of which are incorporated by reference.

Other bioactive agents suitable for inclusion in the devices of the invention include antiproliferative agents, antimitotic agents, antinflammatory agents, anticancer agents, antimicrobial agents, antibiotics, enzymes, immunosuppressives (such as cyclosporine, tacrolimus (FK-506), sirolimus (rapamycin), rapamycin analogs, tacrolimus, everolimus), mTOR inhibitors, paclitaxel, antiplatelet agents, hormones; anticoagulants, fibrinolytic agents, aspirin, angiogenic agents, antisense oligionucleotides, cell cycle inhibitors, inhibitors of matrix metalloproteinases, and combinations thereof. Still other bioactive agents that can be incorporated in or coated on a frame include a PPAR α-agonist, a PPAR δ agonist and RXR agonists, as disclosed in published U.S. Patent publication US2004/0073297, published on Apr. 15, 2004 and incorporated herein by reference. Further examples of bioactive agents suitable for inclusion in the devices of the present invention are disclosed in U.S. Publication Number 2007/0043431, published Feb. 22, 2007, the contents of which are incorporated by reference.

Delivery of the Device

Another aspect of the invention provides methods for delivering the device as described herein to any suitable body vessel, such as a vein, artery, biliary duct, ureteral vessel, bronchial duct, body passage or portion of the alimentary canal. While many preferred embodiments discussed herein discuss implantation of the valve prosthesis in a vein, other embodiments provide for implantation within other body vessels. There are many types of body canals, blood vessels, ducts, tubes and other body passages requiring a flow control device, such as the device of the present invention, and the term "vessel" is meant to include all such passages.

The implantable device of the invention can be percutaneously delivered through a body lumen to a target site. The target site may be, for example, a location in the venous system adjacent to an insufficient venous valve. The delivery system can include a catheter having a distal end adapted for insertion into a body vessel and a proximal end that remains outside the body vessel.

The implantable device can be disposed on the distal end of the catheter or placed within a lumen at the distal end of the catheter. Placement of the implantable device can be performed by inserting the distal end of the catheter into a body vessel and navigating the distal end to a point in a vessel in need of artificial support. The catheter can be placed over a guidewire to facilitate navigation. Once the device is at the point of treatment, it can be released from the catheter and allowed to adopt its expanded state. The catheter can then be withdrawn from the vessel, leaving the device in its expanded state at the point of treatment within the body vessel. Devices of the present invention may be delivered by techniques similar to those disclosed for the delivery of collapsible self-expandable implants in U.S. Pat. No. 5,324,304, issued Jun. 28, 2004, the contents of which are incorporated by reference.

In certain embodiments the hub member is removed after implantation of the device. Removal of the hub member may be performed by cutting the struts to release the hub member. In some embodiments, the hub member can be retrieved using a hook similar to the one depicted in FIG. 1(b).

An appropriately sized delivery catheter can be selected by one skilled in the art for a given application. For example, some medical devices can be delivered using a delivery catheter selected from one or more delivery catheter sizes from the group consisting of: 3, 4, 5, 6, 7, 8, 9, 10, 11, 12, 13, 14, 15, 16, 17, 18, 19, 20, 21, 22, 23 and 24 french (F) delivery catheters, or increments of 0.1 F therebetween. In some embodiments, a delivery catheter sized between 3 and 24 F, or preferably between about 6 F and 16 F can be used.

Methods of Treatment

Other aspects of the invention provide methods of treating a subject, which can be animal or human, by implanting one or more of the devices described herein. In some embodiments, methods of treating may include delivering the device to a point of treatment in a body vessel and deploying a device at the point of treatment. Conditions treated include, but are not limited to venous valve insufficiency, venous valve-related conditions, varicose veins, esophageal reflux, restenosis and atherosclerosis.

Kits Including an Implantable Device

Another aspect of the present invention provides kits comprising the device of the invention. On one embodiment, a kit comprises the device and a delivery catheter. In another embodiment, the kit further comprises sterile packaging material and or instruction material. Such kits may include more than one implantable device. The implantable devices can be of substantially the same size and shape, or, alternatively, can vary with respect to size and shape so as to accommodate placement in body vessels of differing sizes. In such embodiments, the kit may further comprise visible indicia identifying the implantable device as, for example, a venous or other vascular valve or a particular size, and/or can contain or otherwise be associated with printed materials identifying the prosthesis as a venous or other vascular valve and including information concerning its use as a venous or other vascular valve.

Any other undisclosed or incidental details of the construction or composition of the various elements of the disclosed embodiments of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously.

While the invention has been illustrated and described in detail in the drawings and foregoing description, the same is to be considered as illustrative and not restrictive in character, it being understood that only exemplary embodiments have been shown and described and do not limit the scope of the invention in any manner. The illustrative embodiments are not exclusive of each other or of other embodiments not recited herein. Accordingly, the invention also provides embodiments that comprise combinations of one or more of the illustrative embodiments described above. Modifications and variations of the invention as herein set forth can be made without departing from the spirit and scope thereof, and, therefore, only such limitations should be imposed as are indicated by the appended claims.

We claim:

1. A device for implantation in a body vessel, the device having a lengthwise axis and comprising:
   a hub member;
   a plurality of flexible struts, each strut having a first end attached to the hub member and a second end, wherein the struts are spring-biased to diverge from the hub member;
   a frame member extending only partially along a circumference of the device about said lengthwise axis and at an angle with respect to said lengthwise axis from a first attachment point with a first of the plurality of struts to a second attachment point with a second of the plurality of struts, wherein the frame member contacts at least a third of the plurality of struts; and
   a leaflet having a perimeter, a first portion of the perimeter extending along and continuously attached to the frame member from the first attachment point to the second attachment point and a second portion of the perimeter free of contact with the frame member;
   wherein the leaflet is deformable between a first position allowing fluid flow in a first, antegrade direction and a second position restricting fluid flow in a second, retrograde direction.

2. The device of claim 1, wherein the hub member comprises a closed frame defining an aperture.

3. The device of claim 1, the second end of at least one of the plurality of struts having an anchoring mechanism adapted to engage a wall of the body vessel.

4. The device of claim 3, wherein the anchoring mechanism is selected from the group consisting of a barb and a hook.

5. The device of claim 1, wherein the leaflet comprises a material selected from the group consisting of a biocompatible polymer, cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material, polytetrafluoroethylene, polylactic acid, polyglycolic acid, a polyanhydride, polycaprolactone, polyhydroxybutyrate valerate, polyhydroxyalkanoate, a polyurethane, naturally derived or synthetic collagenous material, an extracellular matrix material, submucosa, small intestinal submucosa, stomach submucosa, urinary bladder submucosa, uterine submucosa, renal capsule membrane, dura mater, pericardium, serosa, peritoneum or basement membrane materials, liver basement membrane, a mammalian tissue leaflet, chemically fixed material of a human or non-human primate origin and mixtures and copolymers thereof.

6. The device of claim 1, wherein the leaflet comprises an extracellular matrix material or chemically fixed material of a human or non-human primate origin.

7. The device of claim 6, wherein the leaflet comprises chemically fixed material of a human or non-human primate origin.

8. The device of claim 1, further comprising at least one expanding member extending between two of the plurality of struts, wherein the expanding member connects to each of the two of the plurality of struts between the hub member and the frame member.

9. The device of claim 8, wherein the hub member is biodegradable and wherein the expanding member is adapted to position the struts against the vessel wall when the hub member degrades.

10. The device of claim 8, where the hub member comprises a biodegradable polymer.

11. The device of claim 8, wherein the hub member is detachable from the struts and wherein the expanding member is adapted to position the struts against the vessel wall upon detachment of the hub member.

12. The device of claim 1, wherein the struts comprise a material selected from a group consisting of stainless steel, nickel, silver, platinum, palladium, gold, titanium, tantalum, iridium, tungsten, and a self-expanding nickel titanium alloy.

13. The device of claim 1, wherein the frame member extends distally from each of the first and second attachment points and away from the hub member with respect to said lengthwise axis.

14. The device of claim 1, wherein the frame member has first and second ends;
   wherein the first end is attached to the first of the plurality of struts at the first attachment point; and
   wherein the second end is attached to the second of the plurality of struts at the second attachment point.

15. A device for implantation in a body vessel, the device having a lengthwise axis and comprising:
   a hub member;
   a plurality of struts diverging from the hub member, each strut having a first end attached to the hub member and a second end;
   a graft sheet attached to and extending between portions of a first and a second of the plurality of struts; and
   a frame member extending only partially along a circumference of the device about said lengthwise axis and at an angle with respect to said lengthwise axis from a first attachment point with a first of the plurality of struts to a second attachment point with a second of the plurality of struts, wherein the frame member contacts at least a third of the plurality of struts; and
   a leaflet having a perimeter, a first portion of the perimeter extending along and attaching to the graft sheet and a second portion of the perimeter extending along and continuously attached to the frame member from the first attachment point to the second attachment point;
   wherein the leaflet is deformable between a first position allowing fluid flow in a first, antegrade direction and a second position restricting fluid flow in a second, retrograde direction.

16. The device of claim 15, wherein the hub member comprises a closed frame defining an aperture.

17. The device of claim 15, wherein the graft sheet comprises a material selected from the group consisting of a biocompatible polymer, cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material, polytetrafluoroethylene, polylactic acid, polyglycolic acid, a polyanhydride, polycaprolactone, polyhydroxybutyrate valerate, polyhydroxyalkanoate, a polyurethane, naturally derived or synthetic collagenous material, an extracellular matrix material, submucosa, small intestinal submucosa, stomach submucosa, urinary bladder submucosa, uterine submucosa, renal capsule membrane, dura mater, pericardium, serosa, peritoneum or basement membrane materials, liver basement membrane, mammalian tissue, chemically fixed material of a human or non-human primate origin and mixtures and copolymers thereof.

18. The device of claim 15, wherein the graft sheet comprises an extracellular matrix material or chemically fixed material of a human or non-human primate origin.

19. The device of claim 15, wherein the leaflet comprises a material selected from the group consisting of a biocompatible polymer, cellulose acetate, cellulose nitrate, silicone, polyethylene, teraphthalate, polyurethane, polyamide, polyester, polyorthoester, poly anhydride, polyether sulfone, polycarbonate, polypropylene, high molecular weight polyethylene, a fluoroplastic material, polytetrafluoroethylene, polylactic acid, polyglycolic acid, a polyanhydride, polycaprolactone, polyhydroxybutyrate valerate, polyhydroxyalkanoate, a polyurethane, naturally derived or synthetic collagenous material, an extracellular matrix material, submucosa, small intestinal submucosa, stomach submucosa, urinary bladder submucosa, uterine submucosa, renal capsule membrane, dura mater, pericardium, serosa, peritoneum or basement membrane materials, liver basement membrane, a mammalian tissue leaflet, chemically fixed material of a human or non-human primate origin and mixtures and copolymers thereof.

20. The device of claim 15, wherein the leaflet comprises an extracellular matrix material or chemically fixed material of a human or non-human primate origin.

* * * * *